United States Patent [19]

Böhshar et al.

[11] Patent Number: 5,210,260
[45] Date of Patent: May 11, 1993

[54] PROCESS FOR OBTAINING BIS(2,4-DI-TERT-BUTYLPHENYL) HALOPHOSPHITES

[75] Inventors: Manfred Böhshar, Kelkheim; Hans-Jerg Kleiner, Kronberg, both of Fed. Rep. of Germany

[73] Assignee: Hoechst AG, Frankfurt am Main, Fed. Rep. of Germany

[21] Appl. No.: 856,073
[22] PCT Filed: Nov. 3, 1990
[86] PCT No.: PCT/EP90/01843
 § 371 Date: Jul. 6, 1992
 § 102(e) Date: Jul. 6, 1992
[87] PCT Pub. No.: WO91/07415
 PCT Pub. Date: May 30, 1991

[30] Foreign Application Priority Data

Nov. 11, 1989 [DE] Fed. Rep. of Germany ....... 3937610

[51] Int. Cl.⁵ .............................................. C07F 9/146
[52] U.S. Cl. ...................................................... 558/90
[58] Field of Search ............................................ 558/90

[56] References Cited

U.S. PATENT DOCUMENTS

| | | | |
|---|---|---|---|
| 4,032,602 | 6/1977 | Mazour et al. | 558/90 |
| 4,079,103 | 3/1978 | Mazour | 558/90 |
| 4,118,435 | 10/1978 | Kleinstück et al. | 558/90 |
| 4,739,000 | 4/1988 | Burton | 524/128 |

FOREIGN PATENT DOCUMENTS 0158300 10/1985 European Pat. Off. .

*Primary Examiner*—Joseph Paul Brust
*Assistant Examiner*—Michael G. Ambrose

[57] ABSTRACT

The invention relates to a process for obtaining phosphorus acid-bis(2,4-di-tert-butylphenyl) ester halides in which a phosphorus acid-2,4-di-tert-butylphenyl ester dihalide is heated in the presence of a catalyst containing nitrogen or phosphorus, or both, to 130° C. to 280° C. and the phosphorus trihalide produced by disproportionation is removed from the reaction mixture.

17 Claims, No Drawings

PROCESS FOR OBTAINING BIS(2,4-DI-TERT-BUTYLPHENYL) HALOPHOSPHITES

DESCRIPTION

Bis(2,4-di-tert-butylphenyl) halophosphites are useful starting compounds for the preparation of phosphites (U.S. Pat. No. 4,739,000) or phosphonites (German Patent Applications P 38 43 016.9 and P 39 16 502.7) of industrial interest, which are used as stabilizers for synthetic polymers.

It is known from U.S. Pat. No. 4,739,000 that bis(2,4-di-tert-butylphenyl) chlorophosphite can be prepared by the reaction of phosphorus trichloride with twice the molar amounts of 2,4-di-tert-butylphenol and triethylamine to neutralize the hydrochloric acid liberated. In this process, the use of considerable amounts of a suitable aprotic solvent such as toluene is naturally unavoidable. The final product, according to the information there, has a purity of 85%.

For intended industrial production, such a procedure is particularly unfavorable, because not only do considerable amounts of solvents have to be worked up again, but the triethylammonium chloride formed also has to be neutralized with an alkali metal hydroxide solution in order to recover the base used as auxiliary. A forced yield of 2 equivalents of salt cannot be avoided in this case.

The preparation of diaryl halophosphites by direct reaction of phenols or naphthols and phosphorus trihalides in the molar ratio 2:1 is unsatisfactory because of disproportionation reactions and secondary reactions which cannot be controlled (Houben-Weyl, "Methoden der Organischen Chemie", [Methods of Organic Chemistry], E1, p. 373, 1982, see also Zh. Obsch. Khim. 37, 464–468, 1967).

The object of the present invention was therefore to obtain bis(2,4-di-tert-butylphenyl) halophosphites in a simple manner.

To achieve this object, the invention proposes a process for obtaining bis(2,4-di-tert-butylphenyl) halophosphites of the formula

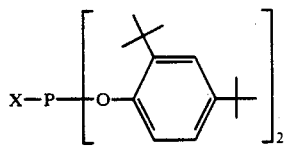

(I)

in which X is a halogen having an atomic weight of at least 35, preferably chlorine or bromine, in particular chlorine, which is characterized in that a 2,4-di-tert-butylphenyl dihalophosphite of the formula (II)

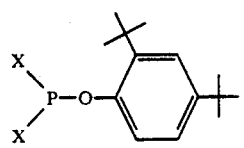

(II)

is heated to 130° to 280° C. in the presence of a catalytically active compound containing nitrogen and/or phosphorus and the phosphorus trihalide formed in this way by disproportionation is removed from the reaction mixture.

According to a particularly preferred embodiment, a procedure is used in which, by addition of a less than stoichiometric amount of 2,4-di-tert-butylphenol, additional bis(2,4-di-tert-butylphenyl) halophosphite is produced.

The process according to the invention is not affected by the disadvantages which are associated with the known process.

The reaction, which can be carried out per se in any conceivable manner, is preferably carried out without the use of a solvent, although it can also be carried out with a solvent which is used as an azeotropic entraining agent. Advantageously, the dihalophosphorous acid monoester (II) is reacted with up to 0.9, preferably 0.3 to 0.6, equivalents of 2,4-di-tert-butylphenol and the mixture is heated in the presence of the catalyst to 130°–280° C. In this process, it is particularly advantageous, after completion of the evolution of hydrogen halide, to additionally carry out a sufficiently long after-reaction in the abovementioned temperature range, the content of (II) being reduced in favor of the product (I) by disproportionation processes without undesired by-products being formed to a noticeable extent. To isolate the desired product (I), residual starting material (II) is then distilled off under reduced pressure. In this process, the catalyst is usually also carried off.

Preferably, the reaction is carried out at temperatures from 160° to 230° C. The reaction is in general complete, depending on the temperature used, after 2 to 10 hours. The reaction is usually carried out in the course of 2 to 5 hours.

Generally, the reaction is carried out under normal pressure; however, it may sometimes be advantageous to favor the removal of the hydrogen chloride by the use of reduced pressure.

As the reactants are sensitive to hydrolysis, the reaction is advantageously carried out with exclusion of moisture. It may be advantageous to carry out the reaction while passing through inert gas such as nitrogen or argon or under a protective gas atmosphere of these gases.

The catalyst is usually employed in small amounts, for example 0.0001 to 0.1 mol, preferably 0.001 to 0.02 mol per mole of (II).

Preferably, the catalysts employed according to the invention are a) compounds of the formulae (III), (IV), (V) or (VI)

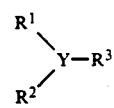

(III)

(IV)

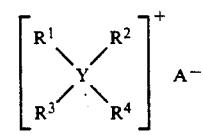

(V)

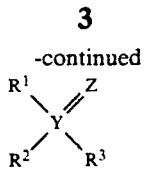

in which Y is an element of the fifth main group of the Periodic Table according to Meyer-Mendeleev having an atomic number from 7 to 15 (i.e. nitrogen or phosphorus), A is an inorganic or organic acid radical, preferably a halide, sulfate or sulfonate, $R^1$, $R^2$, $R^3$ and $R^4$ are identical or different organic radicals, preferably of (cyclo)aliphatic or aromatic character, having up to 20 carbon atoms, preferably 1 to 10 carbon atoms, where two of the radicals $R^1$ to $R^4$ or, in the case of the formula (VI), two or three of the radicals $R^1$ to $R^3$ can close to give a cyclic, optionally substituted system, if appropriate with the inclusion of a heteroatom such as oxygen, nitrogen or sulfur, and Z is oxygen or—if Y is phosphorus —alternatively sulfur, two halogen atoms or the group $NR^5$, where $R^5$ is $R^1$ or hydrogen, b) acid amides and/or c) compounds from the group comprising mono- to tribasic, organic or inorganic fully amidated acids of tri- or pentavalent phosphorus, whose nitrogen atoms are alkyllated by aliphatic radicals having up to 20 carbon atoms, preferably 1 to 10 carbon atoms, and whose organic radicals can contain up to 20 carbon atoms, preferably 1 to 10 carbon atoms.

Examples of suitable catalysts are:

A. Tertiary aliphatic and aromatic amines and phosphines such as trimethyl-, triethyl-, tripropyltriisopropyl-, tributyl-, tri-n-hexyl-, tris(2-ethylhexyl)- and triphenylamine, trimethyl-, triethyl-, tripropyl-, tributyl-, triphenyl- and tris(p-dimethylaminophenyl)phosphine and the corresponding mixed amines, phosphines, phospholanes and phospholenes such as dimethylethylamine, diethylbutylamine, N-dimethylaniline, 4-methyl-N-dimethylaniline, N-diethylaniline, bis-(1,8-dimethylamino)-naphthalene, N,N'-tetramethylphenylenediamine or N-methylpyrrolidine; methyldiethylphosphine,-dimethylpropylphosphine, diethylbenzylphosphine,1-methyl-3-phospholene and 1-ethyl-3-methyl-3-phospholene;

B. Azomethines such as hydrobenzamide, benzylideneaniline, o-, m- and p-methyl-, o-, m- and p-methoxyo-, m- and p-chlorobenzylideneaniline and corresponding derivatives of substituted anilines such as of o-, m- and p-toluidine, of o-, m- and p-nitroaniline, of o-, m- and p-anisidine and of o-, m- and p-chloroaniline;

C. Quaternary ammonium salts or phosphonium salts such as tetramethylammonium chloride or bromide, tetraethylphosphonium chloride, trimethyl- or triethylbenzylammonium chloride or bromide, trimethylbenzylphosphonium chloride, triphenylethylphosphonium-2,4-diaminobenzene sulfonate;

D. Heterocyclic compounds having aromatic character such as pyridine, quinoline, their various alkyl and dialkyl, preferably methyl or dimethyl derivatives, dimethylaminopyridines,imidazole,N-vinylimidazole, benzothiazole, 2-amino-6-ethoxybenzothiazole, and also phosphabenzoles;

E. Acid amides such as dimethylformamide, diethylformamide, N-dimethylacetamide, N-diethylpropionamide, N-dimethylbenzamide, N-methylpyrrolidone, N,N'-tetramethylterephthalamide or ureas such as tetramethylurea and trimethylphenylurea;

F. Other nitrogen and/or phosphorus compounds having a higher valency of a nitrogen or phosphorus atom than 3, such as pyridine-N-oxide, trimethyl-, tributyl-, trihexyl-, triphenyl-, and dimethylphenylphosphine oxide and dimethylchloromethyl-, dimethyleicosyl-, dimethyldodecyl-, dimethyl- and dimethylpyrrolidinyl-1-methylphosphine oxide, triphenylphosphine dichloride, dimethylphenylphosphine sulfide, dimethyldodecylphosphine sulfide, triphenylphosphine imine, dimethylchloromethylphosphine dichloride, N-2-dimethylphosphinylethylmethylacetamide, N-2-dimethylphosphinylcthylmethylamine, phospholeneoxides or phospholane oxides, such as 1-methylphospholene-1-oxide and 1-ethyl-3-methylpholene-1-oxide or 1-methylphospholane-1-oxide and 1-ethyl-3-methylphospholane-1-oxide;

G. Amides of phosphinous and phosphonous acid and of phosphinic and phosphonic acids and their thio analogs, such as ethanephosphonic acid bisdiethylamide, methanebutanephosphinous acid dimethylamide, diethylphosphinous acid isobutylamide, and also triamides of phosphoric acid and thiophosphoric acid, such as hexamethylphosphoric triamide.

Mixtures of catalysts of this type can also be employed.

The 2,4-di-tert-butylphenyl dihalophosphites (II) required as starting substances are known from the literature and can be prepared in a simple manner by the process described in German Application P 39 28 291.0 by reaction of $PX_3$ (X=Cl, Br) with 2,4-di-tert-butylphenol. The starting substances thus obtained can be used directly for the present process. Prior distillation is not necessary.

The reaction product is usually obtained in yellow viscous form. As the main constituent, it contains bis(2,4-di-tert-butylphenyl) halophosphite of the formula (I) in which the content of (I) actually also depends on the chosen ratio of the reactants, the reaction temperature and the reaction time. For working-up, unreacted starting material (II) can be removed by distillation under reduced pressure. The residue then in general has a content of 83 to 97% (according to $^{31}P$-NMR analysis) of (I). If it is desired to react the product (II) with Grignard compounds, as is described in German Patent Applications P 38 43 016.9 and P 39 16 502.7, in order to prepare stabilizers for polymers, then a further purification is not necessary. If desired, the products (I), however, can be further purified by distillation under reduced pressure.

It is particularly suprising that, by the process according to the invention, diaryl monohalophosphites are available in such a high yield, since it is known from the literature that an equilibrium is established with such compounds in the temperature range used as a result of diproportionations, a complex mixture of various products having a very high content of triaryl phosphites being formed (for example Zh. Obsch. Khim. Vol. 37, 464–468, 1967). In order to suppress such reactions, a preferred temperature range of 5° to 100° C. is also given in U.S. Pat. No. 4,739,000 for the preparation of (I) (with X=Cl). In the present case, the formation of a particularly high proportion of tris(2,4-di-tert-butylphenyl) phosphite was therefore also to be expected, because the catalysts used, as is known, catalyze the formation of this by-product, which is undesired in this case (see German Offenlegungsschrift 2,940,620).

In the following examples, the content information relates to the percentage of total phosphorus according to $^{31}$P-NMR analysis.

EXAMPLES

1) A mixture of 768 g (2.5 mol) of 2,4-di-tert-butylphenyl dichlorophosphite, 258 g (1.25 mol) of 2,4-di-tert-butylphenol and 0.2 g of 4-dimethylaminopyridine (=1.6 mmol) was heated to about 180° C. with exclusion of moisture and under a nitrogen atmosphere for 5 hours, a strong evolution of hydrogen chloride taking place at the beginning. The mixture was then allowed to cool to 100° C. and unreacted dichlorophosphorous acid ester and low-boiling components were distilled off under reduced pressure until the internal temperature was 200° C. In the course of this, about 200 g of distillate were obtained. The clear yellow distillation residue had a content of about 88% of bis(2,4-di-tert-butylphenyl) chlorophosphite; δ CDCl$_3$=160.5 ppm.

2) The reaction was carried out as in Example 1, but at 140° C. About 280 g of unreacted starting material were recovered. The distillation residue contained about 85% of bis(2,4-di-tert-butylphenyl) chlorophosphite.

3) As in Example 1, 614.4 g (=2 mol) of 2,4-di-tert-butylphenyl dichlorophosphite and 206.3 g (=1 mol) of 2,4-di-tert-butylphenol were reacted in the presence of 1 g (0.012 mol) of pyridine. 240 g of starting compound were recovered. The distillation residue contained about 90% of bis(2,4-di-tert-butylphenyl) chlorophosphite.

4) The mixture of 921.6 g (3 mol) of 2,4-di-tert-butylphenyl dichlorophosphite and 0.3 g (=2.4 mmol) of 4-dimethylaminopyridine was stirred for 5 hours at 190°-200° C. with exclusion of moisture and while passing through a gentle stream of nitrogen. During this time, about 165 g of phosphorus trichloride distilled off. The mixture was then allowed to cool to about 100° C. and was distilled under reduced pressure and with renewed heating until the bath temperature was 200° C., whereupon about 190 g of virtually pure 2,4-di-tert-butylphenyl dichlorophosphite distilled over.

The yellow viscous distillation residue had a content of about 97% of bis(2,4-di-tert-butylphenyl) chlorophosphite; δ CDCl$_3$=160.5 ppm.

5) The mixture of 92.2 g (=0.3 mol) of 2,4-di-tert-butylphenyl dichlorophosphite and 0.1 g (=0.9 mmol) of 4-dimethylaminopyridine was stirred for 6 hours at 190° C. while passing through a gentle stream of nitrogen. In the course of this, PCl$_3$ formed was carried off. The mixture was allowed to cool, the distillative removal of residual starting material was dispensed with and an $^{31}$P-NMR spectrum was prepared. The residual product contained about 70% of bis(2,4-di-tert-butylphenyl) chlorophosphite.

6) The reaction was carried out as in Example 4 with the difference that 0.1 g (0.5 mmol) of tri-n-butylphosphine was used as the catalyst. The residual product contained about 50% of bis(2,4-di-tert-butylphenyl) chlorophosphite.

COMPARISON EXPERIMENT TO EXAMPLES 5 AND 6

In an experiment carried out under the same conditions, but without addition of catalysts, the content of bis(2,4-di-tert-butylphenyl) chlorophosphite after the same reaction time was only about 4%.

We claim:

1. Process for obtaining bis(2,4-di-tert-butylphenyl) halophosphites of the formula

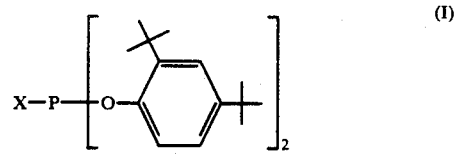

in which X is a halogen having an atomic weight of at least 35, which comprises heating a 2,4-di-tert-butylphenyl dihalophosphite of the formula (II)

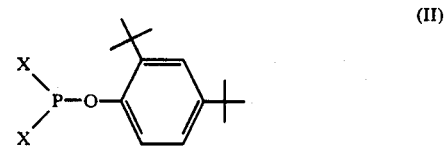

to 130° to 280° C. in the presence of a catalytically active compound containing nitrogen and/or phosphorus and removing the phosphorus trihalide, formed in this way by disproportionation, from the reaction mixture.

2. Process according to claim 1, wherein the removal of the phosphorus trihalide is assisted by passing through a gas which is inert to the reactants.

3. Process according to claim 1 or 2, wherein, by addition of a less than stoichiometric amount of 2,4-di-tert-butylphenol, additional bis(2,4-di-tert-butylphenyl) halophosphite (I) is formed.

4. Process according to claim 3, wherein the 2,4-di-tert-butylphenol is added in an amount of up to 0.9 equivalents per mole of 2,4-di-tert-butylphenyl dihalophosphite.

5. Process according to claim 4, wherein the 2,4-di-tert-butylphenol is added in an amount from 0.3 to 0.6 equivalents per mole of 2,4-di-tertbutylphenyl dihalophosphite.

6. Process according to claim 1, wherein the reaction is carried out without addition of a solvent.

7. Process according to claim 1, wherein the catalyst employed is at least one representative from the group comprising a) compounds of the formulae (III), (IV), (V) or (VI)

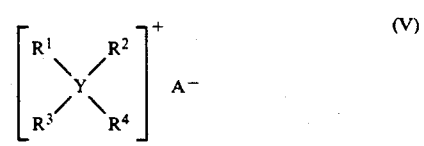

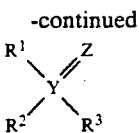

in which Y is an element of the fifth main group of the Periodic Table according to Meyer-Mendeleev having an atomic number of 7 to 15, A is an inorganic or organic acid radical, $R^1$, $R^2$, $R^3$ and $R^4$ are identical or different organic radicals having up to 20 carbon atoms, where two of the radicals $R^1$ to $R^4$ or, in the case of the general formula (VI), two or three of the radicals $R^1$ to $R^3$ can close to give a cyclic system, optionally with the inclusion of a heteroatom such as oxygen, nitrogen or sulfur, and Z is oxygen or—if Y is phosphorus—alternatively sulfur, two halogen atoms or the group $NR^5$, where $R^5$ is $R^1$ or hydrogen, b) acid amides and/or c) compounds from the group comprising mono- to tri-basic organic or inorganic fully amidated acids of tri- or pentavalent phosphorus, whose nitrogen atoms are alkylated by aliphatic radicals having up to 20 carbon atoms and whose organic radicals can contain up to 20 carbon atoms.

8. Process according to claim 7, wherein a tertiary amine is used as the catalyst (III).

9. Process according to claim 1, wherein the catalytically active compound is present in an amount from 0.0001 to 0.1, mol per mole of the 2,4-di-tert-butylphenyl dihalophosphite (II).

10. Process according to claim 1, wherein, to isolate the product (I), residual starting material (II) is subsequently removed by distillation.

11. Process according to claim 7, wherein the reaction is carried out at a temperature from 160° to 230° C.

12. Process according to claim 1, wherein said catalytically active compound is present in a catalytically effective amount which is small, in molar terms, relative to the amount of 2,4-di-tert-butylphenyl dihalophosphite present during said heating step.

13. Process according to claim 12, wherein said catalytically effective amount is about 0.0001 to about 0.1 mol per mole of 2,4-di-tert-butylphenyl dihalophosphite.

14. Process according to claim 13, wherein said catalytically effective amount is about 0.001 to about 0.02 mol per mol of 2,4-di-tert-butylphenyl dihalophosphite.

15. Process according to claim 1, wherein said heating is carried out substantially in the absence of solvent.

16. Process according to claim 15, wherein the compounds present during said heating consist essentially of:

said 2,4-di-tert-butylphenyl dihalophosphite, a catalytic amount, which is small, in molar terms, relative to said 2,4-di-tert-butylphenyl dihalophosphite, of said catalytically active compound, and optionally, an amount, less than a stoichiometric amount relative to said 2,4-di-tert-butylphenyldihalophosphite, of 2,4-di-tert-butylphenol.

17. Process according to claim 16, wherein said amount of 2,4-di-tert-butylphenol is present during said heating.

* * * * *